United States Patent
Jaracz et al.

(10) Patent No.: US 9,354,219 B1
(45) Date of Patent: *May 31, 2016

(54) DETECTING STANNOUS IONS

(71) Applicant: Colgate-Palmolive Company, Piscataway, NJ (US)

(72) Inventors: Stanislav Jaracz, Somerset, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/580,497

(22) Filed: Dec. 23, 2014

(51) Int. Cl.
*G01N 33/20* (2006.01)
*G01N 21/78* (2006.01)
*G01N 21/77* (2006.01)
G01N 21/79 (2006.01)
A61Q 11/00 (2006.01)

(52) U.S. Cl.
CPC ............... *G01N 33/20* (2013.01); *G01N 21/77* (2013.01); *G01N 21/78* (2013.01); *A61Q 11/00* (2013.01); G01N 21/79 (2013.01)

(58) Field of Classification Search
CPC ....... G01N 33/20; G01N 21/77; G01N 21/78; G01N 21/79; Y10T 436/145555; Y10T 436/147777; Y10T 436/18; Y10T 436/20; Y10T 436/200833; Y10T 436/203332; A61Q 11/00
USPC ......... 436/73, 77, 96, 98, 119, 127, 128, 131, 436/164, 166, 171; 422/400, 82.05; 424/49
See application file for complete search history.

(56) References Cited

U.S. PATENT DOCUMENTS

| 4,289,754 A | 9/1981 | Dhabhar et al. |
| 4,992,259 A | 2/1991 | Schiraldi et al. |
| 5,221,626 A * | 6/1993 | Yamazato et al. ............... 436/74 |
| 5,330,748 A | 7/1994 | Winston et al. |
| 6,159,459 A | 12/2000 | Hunter et al. |
| 6,821,786 B2 * | 11/2004 | Rupp ............................ 436/73 |
| 2004/0001897 A1 | 1/2004 | Amano et al. |

(Continued)

FOREIGN PATENT DOCUMENTS

| WO | WO0172347 | 4/2001 |
| WO | WO03/088957 | 10/2003 |
| WO | WO2007/013937 | 2/2007 |

(Continued)

OTHER PUBLICATIONS

Anonymous, "Fluorescent Indicators for Zn2+ and other metal ions", The Molecular Probes Handbook, Life Technologies Inc, http://www.lifetechnologies.com/uk/en/home/references/molecular-probes-the-handbook/indicators-for-ca2-mg2-zn2-and-other-metal-ions/fluorescent-indicators-for-zn2-and-other-metal-ions.html accessed Nov. 13, 2014.

(Continued)

*Primary Examiner* — Maureen Wallenhorst

(57) ABSTRACT

A method of detecting stannous ions that includes providing a zincon-containing indicator having a color, contacting the indicator with a sample, and detecting any resulting change in the color of the indicator, wherein a change in the color of the indicator from the color to colorless indicates that stannous ions are present in the sample. The method is useful for the analysis of oral care compositions. Also provided is the use of zinc on as an indicator for detecting stannous ions.

14 Claims, 1 Drawing Sheet

(56) References Cited

U.S. PATENT DOCUMENTS

2010/0099195 A1* 4/2010 Frederickson .............. 436/81
2014/0024010 A1  1/2014 Akashi et al.

FOREIGN PATENT DOCUMENTS

| WO | WO2008/041055 | 4/2008 |
|---|---|---|
| WO | WO2011028878 | 3/2011 |
| WO | WO2011108300 | 9/2011 |
| WO | WO2011/016984 | 10/2011 |

OTHER PUBLICATIONS

Anonymous, Standard Electrode Potential (data page), http://en.wikipedia.org/wiki/Standard_electrode_potential_(data_page), accessed Nov. 13, 2014.

Areco et al.,, 2007, "Zinc Biosorption by Seaweed Illustrated by the Zincon Colorimetric Method and the Langmuir Isotherm", Journal of Chemical Education, vol. 84, No. 3, pp. 302-305.

Brading et al., 2009, "Gum health benefits of a silica based fluoride toothpaste containing zinc citrate, potassium citrate, hydroxyapatite and vitamin E acetate", International Dental Journal, 59, pp. 332-337.

Brophy et al., 2012, "Calcium ion gradients modulate the zinc affinity and antibacterial activity of human calprotectin", J Am Chem Soc, 134, 43, pp. 18089-18100.

Chen et al., 2001, "Catalytic selenols couple the redox cycles of metallothionein and glutathione", European Journal of Biochemistry, 268, 3346-3353.

Clever et al., 1992, "The Solubility of Some Sparingly Soluble Salts of Zinc and Cadmium in Water and in Aqueous Electrolyte Solutions", J Phys Chem Ref Data, 21, 5, pp. 941-966.

Ejnik et al., 2010, "Mechanism of Cadmium Ion Substitution in Mammalian Zinc Metallothionein and Metallothionein Alpha Domain; Kinetic and Structural Studies", Inorg. Chem., 49, pp. 6525-6534.

Gulson et al., 2010, "Small amounts of zinc from zinc oxide particles in sunscreens applied outdoors are absorbed through human skin", Toxicological Sciences, 118, 1, pp. 140-149.

Harrap et al., 1984, "Human oral retention of zinc from mouthwashes containing zinc salts and its relevance to dental plaque control", Archs Oral Biol, 29, 2, pp. 87-91.

He et al., 2002, "Inhibitory effect of $ZnCl_2$ on glycolysis in human oral microbes", Archs Oral Biol, 47, 2, pp. 117-129.

Klemm, 2011, "Microelectrochemical characterization of Zn, ZnO and Zn—Mg alloys with online dissolution monitoring", Ruhr University Bochum, Germany.

Mabrouk et al., 1992, "Direct electrochemical synthesis of cobalt, nickel, copper, zinc, cadmium, tin and lead complexes", Trans Met Chem, 17, pp. 1-4.

Mitra et al., 1960, "The reaction between polyvalent metal cations and alkali metal pyrophosphates" Proc Nat Inst Sci India, 26A, pp. 151-161.

Morozova et al., 1976, $Zn_2P_2O_7$—$K_4P_2O_7$—$H_2O$ System at 25°, . J Inorg Chem, 12(6):878.

Nevitt et al., 1958, "Topical applications of sodium fluoride and stannous fluoride", Public Health Rep, vol. 73, No. 9, pp. 847-850.

Ozedimir et al., 1998, "The Determination of Salivaiy Zinc Level Following Delivery from Zinc Containing Toothpaste", Tr. J. of Medical Sciences, 28, pp. 281-283.

Rakhmatullina et al., 2013, "Inhibition of enamel erosion by stannous and fluoride containing rinsing solutions", Schweiz Monatsschr Zahnmed, vol. 123, pp. 192-197.

Richter et al., 2002, "Solid phase spectrophotametric determination of copper in water by using immobilized zincon in a sephadex A25 resin", Anal. Lett. 35, pp. 635-646.

Skog et al., 1964, "A comparative investigation of the pereutaneous absorption of metal compounds in the guinea pig by means of radioactive isotopes: 51Cr, 58Co, 65Zn, 110mAg, 115mCd, 203Hg", J Invest Dermatol, 43, 3, pp. 187-192.

Thompson, 1989. "Chapter 22: Zinc Links: Coordination Chemistry and Nutritional Deficiency" in "Chemtrek Small Scale Experiments for General Chemistry", Prentice Hall, NJ, USA.

Wilcox, 2009, "The black and white of immersion tin: keeping an eye on cupric ions can eliminate black tin", Printed Circuit Design & Fab, Jul. 1, 2009.

Yoe et al., 1952, "A new colorimetric reagent for zinc", Anal. Chim. Acta, vol. 6, pp. 526-527.

Zhang et al., 2009. "Effect of resveratrol and zinc on intracellular zinc status in normal human prostate epithelial cells", Am J Physiol Cell Physiol, 297, C632-C644.

* cited by examiner

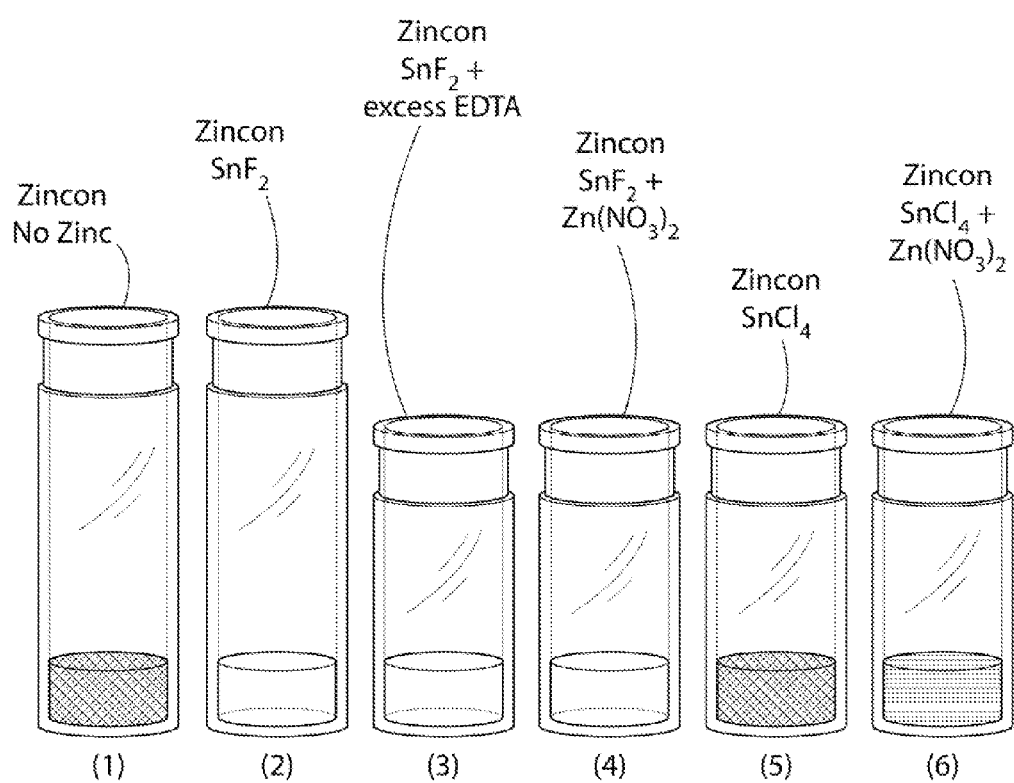

DETECTING STANNOUS IONS

TECHNICAL FIELD

The present invention generally relates to methods for detecting stannous ions, particularly to methods for detecting stannous ions in oral care compositions, and to the use of an indicator to detect stannous ions.

BACKGROUND

Stannous ions ($Sn^{2+}$) are used in oral care compositions because they display biocidal activity and are effective in preventing dental erosion (Rakhmatullina et al, 2013. "Inhibition of enamel erosion by stannous and fluoride containing rinsing solutions", Schweiz Monatsschr Zahnmed, vol. 123, pp. 192-197). Aqueous solutions comprising stannous ions have been reported to be unstable (Nevitt et al, 1958. "Topical applications of sodium fluoride and stannous fluoride", Public Health Rep, vol. 73, no 9, pp. 847-850). Stability is an important property to assess when formulating an oral care composition. There is therefore a need in the art for methods of testing oral care compositions for the presence of stannous ions.

Existing methods for analysing oral care compositions include the measurement the total amount of tin present in the composition. However, not all forms of tin are therapeutically active. In particular, stannic (tin (IV)) ions are believed to be inactive. The existing methods do not discriminate between the various forms of tin. There is therefore a need in the art for a method for the selective detection of stannous ions.

WO2008/041055 discloses oral care compositions comprising a stannous ion source, a polyvalent cation source and a mineral surface active agent. A method of investigating the binding of stannous is also outlined. In this method, the stannous is provided in the form of stannous fluoride. The binding of stannous is estimated by potentiometric detection of available ionic fluoride. Hence, this method does not directly detect the presence of stannous ions.

BRIEF SUMMARY

In one aspect, the present invention provides a method of detecting stannous ions in a sample, which method comprises (i) providing an indicator having a UV/visible absorbance spectrum; (ii) contacting the indicator with a sample, such that if stannous ions are present in the sample, stannous ions react with the indicator; and (iii) detecting a change in the UV/visible absorbance spectrum of the indicator to determine whether stannous ions are present in the sample; wherein the indicator is zincon or a salt thereof. Zincon (o-[α-(2-hydroxy-5-sulfophenyl azobenzylidene hydrazino]benzoic acid, CAS no. 62625-22-3) has surprisingly been found that zincon reacts rapidly and highly selectively with stannous ions. The resulting complex has a different UV/vis absorbance spectrum to free zincon. The present method thereby provides a simple, rapid method of detecting stannous ions.

Step (iii) may comprise detecting a change in the colour of the indicator. A change in the colour of the indicator corresponds to a change in the absorbance of the indicator in the region of the spectrum visible to the human eye (i.e. at wavelengths in the range 390 to 730 nm). Zincon is a brightly coloured dye which appears red when it is present in an aqueous solution at a pH in the range 7 to 10. The complex of zincon with stannous appears colourless under these conditions. The presence of stannous ions may therefore be readily detected by simple visual inspection. The use of detection means, such as a UV/visible spectrometer or a colourimeter, is also contemplated herein.

The detection of stannous ions may be qualitative, and may comprise observing the colour of the indicator. Qualitative detection is generally rapid, simple, and typically requires only a small amount of indicator. Alternatively, the detection may be quantitative. Quantitation may be achieved by titration. The skilled artisan will be familiar with titration methods.

The nature of the sample is not particularly limited. The sample may comprise an oral care composition. Oral care compositions may comprise stannous ions and/or zinc ions as active ingredients, and the methods described herein provide a convenient way of detecting the presence of these ions. The method may be used, for example, during the formulation of new oral care compositions and for shelf-life determinations. Further applications include quality control and quality assurance.

The nature of the oral care composition is not particularly limited. The oral care composition may be, for example, a toothpaste, a tooth gel, a tooth powder, or a mouth rinse. The oral care composition may comprise toothpaste; in this arrangement, the sample may be formed by dispersing the toothpaste in water.

Step (ii) may comprise forming a liquid comprising the indicator, the sample, and water wherein the zincon is dissolved in the liquid. The liquid may comprise a solution. The liquid may include suspended material. Zincon is soluble in water, and providing a liquid in this way is a straightforward way of achieving good contact between the zincon and the sample.

The amount of the indicator present in the liquid is advantageously no greater than 500 ppm by weight of the liquid, and may be in the range of 30 to 60 ppm by weight of the liquid. Dilute solutions of zincon provide good sensitivity, because fewer stannous ions are required to produce a colour change.

In the arrangements where step (ii) comprises forming a liquid, the method may comprise titrating the sample with a solution of the indicator. Titration allows quantitative measurement of the amount of stannous present in the sample, but may require a large amount of zincon to be used.

The liquid may have a pH in the range of 5 to 10. The reaction between stannous ions and zincon was found to proceed well under these pH conditions.

The pH of the liquid may be in the range 6.3 to 7.3. This pH range approximates the pH range found in the oral cavity (Afraiman et al, 2006. "The distribution of oral mucosal pH values in healthy saliva secretors", Oral Dis, 12, 4, pp 420-423). Thus, the delivery of stannous ions under biorelevant conditions may be investigated.

The pH range may alternatively be in the range of 7 to 10. This is representative of the pH ranges used in typical oral care compositions, which are often mildly alkaline. Tests which operate under these pH conditions are therefore particularly advantageous. The pH range of 7 to 10 is also preferable in the arrangements where zinc ions are to be detected, because the reaction between zincon and zinc ions is sensitive to pH. In the arrangements where zinc ions are to be detected, the pH is most preferably in the range 9 to 9.5.

The sample may include zinc ions. Zinc has been reported to form a dark blue complex with zincon (Yoe and Rush, 1952. "A new colorimetric reagent for zinc", Anal. Chim. Acta. vol. 6, pp 526-527). Surprisingly, zincon reacts selectively with stannous ions. The colourless stannous complex is formed even in the presence of zinc ions. Zinc ions are often included in oral care compositions. It is therefore useful to be able to detect stannous ions in the presence of zinc ions.

The method may comprise, if stannous ions are detected in the sample, oxidizing the stannous ions to form stannic ions ($Sn^{4+}$); and allowing the zinc ions to react with the indicator. It has been found that zincon binds zinc ions in preference to stannic ions. By oxidizing stannous ions to stannic ions in situ, the zincon may be used to detect both zinc ions and stannous ions in a single assay. This simplifies analysis of the sample.

The stannous ions may be oxidized to stannic ions using any conventional method. An electrochemical technique or an oxidizing agent may be used. The preferred oxidizing agent is hydrogen peroxide. Hydrogen peroxide is readily available commercially, and reacts rapidly with stannous ions. For safety and ease of handling, the hydrogen peroxide may be provided in the form of an aqueous solution. The aqueous solution may comprise hydrogen peroxide in an amount in the range 1% to 5% by weight of the solution. Alternatively, the oxidizing agent may be oxygen from the atmosphere. Allowing a solution comprising stannous ions to stand in air may allow the stannous ions to oxidise. This has the advantage of not requiring the use of any further reagents.

In the arrangements wherein zincon zinc is formed, the concentration of the zincon zinc may be measured by colorimetry. It is often desirable to quantify the amount of zinc ions released by an oral care composition. Because zincon binds to zinc weakly, only the free zinc ions will be detected. This allows the bioavailability of the zinc to be estimated.

In another aspect, the present invention provides the use of zincon as an indicator for detecting stannous ions. Zincon forms a colourless complex with stannous ions, and binds to stannous ions selectively. Zincon is therefore useful for detecting stannous ions in complex mixtures, such as oral care compositions.

The stannous ions may be detected even in the presence of zinc ions. Although zincon has been reported to form a blue complex in the presence of zinc ions, zincon binds stannous ions in preference to zinc ions. Oral care compositions may comprise both stannous ions and zinc ions. It is therefore useful to be able to detect stannous ions in the presence of zinc ions.

The use may be additionally for detecting zinc ions. Contacting zincon with stannic ions does not produce a colour change, and it is therefore believed that zincon does not form a complex with stannic ions. By oxidizing stannous ions to stannic ions subsequent to the detection of the stannous ions, any zinc ions which are present may be detected.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, in which:

FIG. 1 shows a photograph of vials containing the test solutions described in Example 1.

DETAILED DESCRIPTION

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the term "zincon" refers to o-[α-(2-hydroxy-5-sulfophenyl azo)-benzylidene hydrazino]benzoic acid, which has CAS number 56484-13-0. The structure of the sodium salt of zincon is shown below:

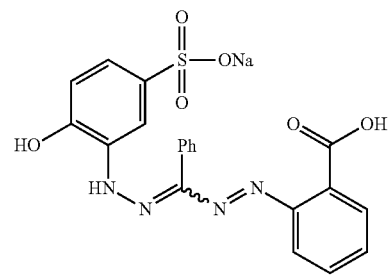

The term "stannous ions" refers to tin (II) ions, i.e. $Sn^{2+}$. The term "stannic ions" refers to tin (IV) ions, i.e. $Sn^{4+}$. The term "zinc ions" refers in particular to zinc (II) ions, i.e. $Zn^{2+}$.

Zincon has been reported to form complexes with copper, cobalt, nickel and iron (Yoe and Rush, 1952. "A new colorimetric reagent for zinc", Anal. Chim. Acta, vol. 6, pp 526-527). The use of zincon to detect cupric (copper (II)) ions in immersion tin plating operations has also been reported (Wilcox, 2009. "The black and white of immersion tin: keeping an eye on cupric ions can eliminate black tin". Printed Circuit Design & Fab, 1 Jul. 2009).

The electrochemical synthesis of a tin zincon complex has also been reported (Mabrouk et al, 1992. "Direct electrochemical synthesis of cobalt, nickel, copper, zinc, cadmium, tin and lead zincon complexes", Trans. Met. Chem., 17, pp 1-4). The complex obtained by this method is described as red-brown. The colourless complex formed in the methods of the present invention is not identified.

The present invention is based on the surprising finding that zincon reacts rapidly and specifically with stannous ions to produce a colourless complex. As shown in FIG. 1 and discussed in detail in the Examples, the colourless complex is formed even in the presence of strong chelating agents and other metal ions such as zinc. Zincon is therefore useful for detecting stannous ions even in complex mixtures, such as oral care compositions.

Notably, zincon does not undergo a colour change when contacted with stannic ions. Without wishing to be bound by theory, it is believed that stannic ions do not react with zincon, at least under the conditions used in the Examples. If such a reaction does occur, then the binding of stannic ions by zincon is weak, because the presence of stannic ions did not prevent the formation of a zinc-zincon complex. The selective detection of stannous ions is important. This is because, unlike stannous ions, stannic ions are not believed to display useful therapeutic activity. The selectivity of zincon for stannous ions renders zincon particularly useful for the analysis of oral care compositions.

Accordingly, in one aspect the present invention provides a method of detecting stannous ions in a sample, which method comprises: (i) providing an indicator having a UV/visible absorbance spectrum; (ii) contacting the indicator with a sample such that if stannous ions are present in the sample, stannous ions react with the indicator, and (iii) detecting a change in the UV/visible absorbance spectrum of the indicator to determine whether stannous ions are present in the sample; wherein the indicator is zincon or a suitable salt thereof.

Zincon reacts rapidly and selectively with stannous ions. This reaction produces a characteristic colour change. The presence of stannous ions may therefore be detected. The present method therefore provides a cost effective technique for directly detecting the presence of stannous ions.

The indicator is zincon or a suitable salt thereof. Zincon is an ionizable compound. Zincon may therefore be provided in the form of a salt. The counterion present in the salt is selected such that the counterion does not interfere with the detection of stannous ions. Suitable salts may be identified for example by contacting the salt with a solution known to contain stannous ions. If a colourless complex is formed, that is, if a colour change to colourless occurs, then the counterion is suitable. A preferred salt is zincon monosodium, which is commercially available. The copper (II) salt of zincon is generally not a suitable salt.

The indicator may be supplied in the form of a composition which is a solution comprising the zincon, a solvent and optionally one or more additives. Zincon is poorly soluble in many organic solvents. The solvent therefore preferably comprises water. Examples of suitable solvents include water and aqueous cosolvent mixtures, for example mixtures comprising water and an alcohol or a ketone. Useful alcohols include C1 to C4 linear or branched alkyl alcohols, such as methanol, ethanol, and isopropanol. Useful ketones include acetone and the like.

In the arrangements where the solvent comprises water, the pH of the solution may be in the range of 5 to 10, preferably 7 to 10, more preferably 9 to 9.5. Zincon has acidic functional groups which become ionized at alkaline pH. Providing a solution which is mildly alkaline therefore assists in dissolving the zincon and facilitates the reaction of zincon with positively-charged metal ions.

The solution may comprise a buffer for maintaining the pH within the desired range. One of skill in the art will be familiar with aqueous buffer solutions. The buffer preferably does not comprise a chelating agent. In some arrangements, zincon is used additionally to detect zinc ions. Zinc ions are bound by zincon weakly, and the presence of chelating agents may therefore interfere with their detection. Examples of useful buffers include ammonium buffer, suitably at a pH in the range of 9 to 9.5; TRIS, suitably at a pH in the range of 7 to 8.5, and HEPES, suitably at a pH in the range of 7 to 7.5.

The amount of zincon present in the indicator composition preferably does not exceed 2% by weight of the indicator composition. For example, zincon may be present in the indicator composition in an amount in the range 0.01% to 1% optionally 0.1% to 1% by weight of the indicator composition. As will be discussed below, it is advantageous to use concentrations of zincon below 500 ppm for detecting stannous ions. Indicator compositions comprising zincon in an amount in the range of 0.01% to 1% by weight may be conveniently diluted by addition to a sample to obtain a concentration of zincon below 500 ppm.

Other components may be included in the indicator composition. Examples of such components include preservatives for extending shelf life. Viscosity modifiers, such as xanthan gum, are also tolerated but are preferably absent.

The method further includes the step of contacting the indicator with a sample. The nature of the sample is not particularly limited.

The sample may comprise an aqueous solution. The aqueous solution may have a pH in the range of 5 to 10, optionally 7 to 10, and preferably 9 to 9.5. It has been found that the reaction between stannous ions and zincon proceeds rapidly under these conditions. The pH range of 7 to 10 is also representative of the conditions present in a typical oral care composition.

The pH of the aqueous solution may alternatively be in the range of 6.3 to 7.3. This approximates the pH range typically encountered in the oral cavity.

The sample preferably comprises an oral care composition. The oral care composition may be, for example, a toothpaste, a tooth gel, a tooth powder or a mouth rinse. If the oral care composition is a toothpaste, a tooth gel, or a tooth powder then the oral care composition is suitably dispersed in a solvent. The solvent is suitably water. For example, the sample may be an aqueous dispersion comprising the oral care composition in an amount in the range 10% to 30% by weight of the dispersion. Preferably, the sample is colourless and/or is substantially free of colourants. This allows the colour change of the indicator to be observed more easily. However, the presence of colourants is tolerated because free zincon is strongly coloured. This means that the colour change of the zincon indicator is detectable even if a background colour is present. In the arrangements where a colourant is present, the change in the UV/visible absorbance of zincon is advantageously detected by visual inspection.

The sample is advantageously substantially free of cupric (copper (II)) ions. Cupric ions have been found to bind zincon even more strongly than stannous ions, forming a bright blue complex. The term "substantially free" is used to mean that the concentration of cupric ions is such that the cupric ions do not interfere with the detection of stannous. Cupric ions are preferably completely absent, but may be present in an amount no greater than 5 ppm. Oral care compositions generally do not comprise cupric ions.

The sample and the indicator are contacted such that the zincon present in the indicator is capable of reacting with stannous ions present in the sample. Typically, the sample comprises a liquid and/or the zincon is supplied in an indicator composition which is a liquid.

A liquid indicator composition may be contacted with a sample by dropwise addition of an indicator composition to the sample. Alternatively, an indicator composition may be sprayed onto the sample.

The sample may include zinc ions. The strong binding of stannous ions by zincon allows the detection of stannous ions even in the presence of zinc ions. In this arrangement, the method optionally further comprises detecting the zinc ions, for example by colourimetry. Detecting the presence of both zinc ions and stannous ions using a single indicator allows for the rapid analysis of an oral care composition.

The zinc ions may be detected by oxidizing the stannous ions to form stannic ions. This allows the zinc ions to react with the zincon to form a zincon-zinc complex. The zincon zinc complex is blue in colour. The colour change to blue allows the detection of the zinc ions. As will be shown in the Examples, zinc ions may be detected in the presence of stannic ions using zincon.

The method advantageously comprises adding an additional amount of indicator to the sample after the stannous ions are oxidized to stannic ions. Zincon may be degraded by oxidising agents over time. Adding further zincon therefore allows zinc to be detected more reliably.

The stannous ions may be oxidized to form stannic ions using any conventional technique. Methods for oxidizing metal ions include electrochemical techniques and the use of chemical oxidizing agents. Examples of oxidizing agents useful in the present methods include atmospheric oxygen; peroxides such as hydrogen peroxide; peracetic acid; persulfates such as sodium persulfate and potassium persulfate; hypochlorites such as sodium hypochlorite; chlorates; perchlorates; iodates; periodates; bromates; perbromates; iodine; and bromine.

A preferred oxidizing agent is hydrogen peroxide. Hydrogen peroxide reacts rapidly with stannous ions, and is readily commercially available. For safety and ease of handling, the hydrogen peroxide may be supplied as an aqueous solution, for example an aqueous solution including 1% to 5% hydrogen peroxide by weight of the aqueous solution.

A further preferred oxidizing agent is atmospheric oxygen. Atmospheric oxygen typically produces a slow oxidation of stannous ions to stannic ions, but has the advantage that no additional reagents are required. For example, stannous ions may be oxidized to stannic ions by allowing the stannous ions to stand in air for 24 hours or more.

Since the oxidation of stannous ions to stannic ions by oxygen from the air is slow, the methods described herein may be carried out in air. If desired, the methods may of course be carried out under an inert gas. Examples of useful inert gases include nitrogen and argon.

The method includes detecting a change in the UV/visible absorbance spectrum of the indicator.

The change in the UV/visible absorbance spectrum arising from the reaction between zincon and stannous ions is such that it produces a colour change which is visible to the human eye. The change is perceivable as a change from red to colourless. Thus, step (iii) most conveniently comprises detecting a change in the colour of the indicator, for example, by visual observation. This has the advantage of not requiring any particular instrumentation.

The use of a spectrometer or colourimeter to carry out step (iii) is also contemplated herein. The precise nature of the changes to the UV/visible absorbance spectrum may be readily determined by routine experimentation and will not be set out in detail here. Reductions in absorbance readings within the visible region (390 to 730 nm) are to be expected in the presence of stannous ions. One of skill in the art will be familiar with the use of spectrometers and colourimeters, and with methods of preparing samples for these instruments. The detection may be quantitative or qualitative. Qualitative detection generally comprises simple visual inspection of the indicator. Quantitative detection may be achieved, for example, by titration. The skilled artisan will be familiar with suitable titration methods.

In the arrangements where the presence of zinc is investigated, the method may comprise measuring the concentration of the zincon zinc complex by colourimetry. Since the binding of zinc by zincon is relatively weak, the presence of chelating agents which render the zinc unavailable and would lead to a reduction in the measured zinc concentration. In this way, determining the amount of zinc present by using zincon provides an estimate of the bioavailable zinc present in the composition.

In another aspect, there is provided the use of zincon as an indicator for detecting stannous ions. As noted above, zincon undergoes a colour change to colourless when it reacts with stannous ions. This allows the detection of stannous ions using zincon. Stannous ions may be detected in the presence of zinc ions. In this arrangement, the zincon may be further used to detect the zinc ions. Generally, the stannous ions will be detected using the zincon, and then the stannous ions will be oxidized to stannic ions to allow the detection of the zinc ions.

EXAMPLES

The present invention will now be explained by reference to the following non-limiting Examples.

Example 1

Detection of Stannous Ions

The behaviour of zincon in the presence of zinc ions, stannous ions, and stannic ions was investigated. Contacting a zincon indicator solution with stannous ions resulted in a colour change from red to colourless. This colour change was observed even in the presence of zinc (II) ions, which have been reported to produce a blue complex with zincon. The inclusion of EDTA in a solution of zincon and stannous ions did not prevent the colour change from occurring. This indicates that zincon may be used to detect stannous ions, even in the presence of other materials.

An indicator was prepared by dissolving zincon sodium salt in a 0.2 M ammonia buffer. The pH of the buffer was 9.25. The amount of zincon sodium salt present in the indicator was 0.3% by weight. A series of test solutions was then prepared. Each test solution included 2 to 3 mL of deionised water, 1 mL of ammonia buffer, and 40 µL of the indicator solution. The remaining components of the solution are set out in Table 1:

TABLE 1

| solutions investigated | |
|---|---|
| | Additive |
| Solution 1 | None |
| Solution 2 | 20 µL of 0.25M $SnF_2$ |
| Solution 3 | 20 µL of 0.25M $SnF_2$ and excess EDTA |
| Solution 4 | 20 µL of 0.25M $SnF_2$ and 20 µL of 0.25M $Zn(NO_3)_2$ |
| Solution 5 | 20 µL of 0.24M $SnCl_4$ |
| Solution 6 | 20 µL of 0.24M $SnCl_4$ and 20 µL of 0.25M $Zn(NO_3)_2$ |

The solutions were stirred to mix the components. A photograph of the resulting solutions is shown in FIG. 1. Vials containing solutions 1 to 6 are shown from left to right.

Solution 1, zincon in the absence of metal ions, was found to have a red colour. The addition of stannous ions, in the form of stannous fluoride, to zincon resulted in the formation of a colourless solution (solution 2). Mixtures of stannous ions with either the strong chelating agent EDTA (solution 3) or zinc (II) ions (solution 4) also resulted in the formation of a colourless solution. This shows that stannous ions are bound strongly by zincon. Accordingly, zincon may be used to detect the presence of stannous ions even when further materials are present.

No colour change was observed when stannic ions were added to zincon (solution 5). A colour change from red to blue was observed when zincon was contacted with a mixture of stannic ions and zinc (II) (solution 6). This colour change is consistent with the formation of a blue zincon zinc complex, as reported by Yoe and Rush (Yoe and Rush, 1952. "A new colorimetric reagent for zinc", Anal. Chim. Acta, vol 6, pp 526-527). This indicates that zincon does not react with stannic ions.

Example 2

Detection of Stannous Ions in the Presence of Zinc Ions

The stannous ion and zinc ion content of a series of commercially available toothpaste compositions were investigated using Zincon. As shown in Example 1, Zincon binds stannous ions in preference to zinc ions but does not bind stannic ions. It has been found that the zinc content of a composition comprising zinc ions and stannous ions may be investigated by oxidising the stannous ions to stannic ions in situ. Hence, both zinc ions and stannic ions may be detected in a single assay using a single indicator.

A Zincon indicator was prepared in accordance with Example 1. Three commercially available toothpaste compositions were then investigated using the following method:
1. Disperse completely 0.5 g of the toothpaste in 2 mL of deionised water.
2. Add 1 mL of 0.2 M ammonia buffer (pH 9.25).
3. Add 40 mL of zincon indicator solution and stir briefly. If the solution becomes colourless, dissolved stannous ions are present, if the solution turns blue, stannous is absent and dissolved zinc is present, and if the solution remains red, there is neither dissolved stannous nor dissolved zinc.
4. If the solution is colourless, add 100 µL of 3% hydrogen peroxide and stir for 2 minutes to oxidize stannous to stannic.
5. Add 40 µL of 0.3% zincon. If the solution turns blue, zinc is bioavailable, if red, zinc is not bioavailable (or absent). Any shade in between means partially bioavailable zinc.

The toothpastes which were investigated are listed in Table 2:

TABLE 2

| toothpaste compositions investigated | |
| --- | --- |
| Composition | Active metal ion source |
| Composition A | 0.454% $SnF_2$ |
| Composition B | 1.07% $SnCl_2$ |
| Composition C | 0.439% $SnF_2$, 0.5% zinc lactate dehydrate, high water |

All percentages given in the table above are by weight of the composition.

Stannous ions were detected in Composition A and Composition B. No stannous ions were detected in Composition C, indicating that this formulation did not provide soluble stannous ions or that the stannous ions had oxidised during storage to yield stannic ions. The zinc was detected in Composition C.

What is claimed is:

1. A method of detecting stannous ions in a sample, which method comprises:
    (i) providing an amount of an indicator comprising zincon or a salt thereof having a UV/visible absorbance spectrum;
    (ii) contacting the indicator with a sample such that if stannous ions are present in the sample, stannous ions react with the indicator; and
    (iii) detecting a change in the UV/visible absorbance spectrum of the indicator to determine whether stannous ions are present in the sample.

2. The method of claim 1, wherein step (iii) comprises detecting a change in the colour of the indicator.

3. The method of claim 1, wherein the sample comprises an oral care composition.

4. The method of claim 3, wherein the oral care composition comprises a toothpaste.

5. The method of claim 1, wherein step (ii) comprises forming a liquid comprising the indicator, the sample, and water.

6. The method of claim 5, wherein the amount of the indicator present in the liquid is no greater than 500 ppm by weight of the liquid.

7. The method of claim 6, wherein the amount of the indicator present in the liquid is in the range of 30 to 60 ppm by weight of the liquid.

8. The method of claim 5, comprising titrating the sample with a solution of the indicator.

9. The method of claim 5, wherein the Liquid has a pH in the range of 5 to 10.

10. The method of claim 9, wherein the liquid has a pH in the range of 6.3 to 7.3.

11. The method of claim 9, wherein the liquid has a pH in the range 7 to 10.

12. The method of claim 11, wherein the sample includes zinc ions.

13. The method of claim 12, wherein stannous ions are present in the sample, and wherein the method further comprises:
    oxidizing the stannous ions after step (iii) to form stannic ions; and
    allowing the zinc ions to react with the indicator.

14. The method of claim 13, subsequently comprising measuring the concentration of the zinc by colourimetry.

* * * * *